United States Patent [19]

Carson et al.

[11] Patent Number: 5,241,969
[45] Date of Patent: Sep. 7, 1993

[54] CONTROLLED AND SAFE FINE NEEDLE ASPIRATION DEVICE

[76] Inventors: Jay W. Carson, 1550 Sorrel Ct., Walnut Creek, Calif. 94598; Curtis T. Thompson, 200 Warren Dr., San Francisco, Calif. 94131

[21] Appl. No.: 896,391

[22] Filed: Jun. 10, 1992

[51] Int. Cl.⁵ .................................... A61B 10/00
[52] U.S. Cl. ................................ 128/753; 128/765; 604/117; 604/227
[58] Field of Search ............ 128/749, 752, 753, 763, 128/765, 766; 604/187, 207, 208, 210, 218, 227, 228, 240, 198, 117, 192, 263; 222/325, 327, 309, 470, 471

[56] References Cited

U.S. PATENT DOCUMENTS

| | | | |
|---|---|---|---|
| 2,047,010 | 7/1936 | Dickinson | 604/117 |
| 2,705,949 | 4/1955 | Silverman | 604/117 |
| 3,530,785 | 9/1970 | Peters | 604/208 |
| 3,538,916 | 11/1970 | Wiles | 604/117 |
| 3,819,091 | 6/1974 | Hollender | 222/327 |
| 4,083,370 | 4/1978 | Taylor | 604/117 |
| 4,594,073 | 6/1986 | Stine | 604/187 |
| 4,619,272 | 10/1986 | Zanibelli | 128/753 |
| 4,711,250 | 12/1987 | Gilbaugh, Jr. et al. | 128/765 |
| 4,846,809 | 7/1989 | Sims | 604/198 |
| 4,998,924 | 3/1991 | Ranford | 604/798 |
| 5,108,408 | 4/1992 | Lally | 604/119 |
| 5,115,816 | 5/1992 | Lee | 128/749 |

FOREIGN PATENT DOCUMENTS 278247 8/1988 European Pat. Off. ............ 604/192
780008 7/1957 United Kingdom ................ 604/117

OTHER PUBLICATIONS

E. Chu and R. Hoye: The clinician and cytopathologist evaluate fine needle aspiration cytology, ACTA CYTOLOGICA vol. 17; 413-417 p. Oct. (1973).
L. Schour and E. Chu: Fine needle aspiration in the management of patients with neoplastic disease, ACTA CYTOLOGICA vol. 18: 472-476 Nov. (1974).

*Primary Examiner*—Stephen C. Pellegrino
*Assistant Examiner*—Guy V. Tucker
*Attorney, Agent, or Firm*—Glen R. Grunewald

[57] ABSTRACT

A syringe holder which is uniquely designed for the diagnostic technique of fine needle aspiration used in the diagnosis of cancer and other pathological processes. The holder can be used repeatedly with a standard disposable syringe (42) and needle (44). A stabilizing ring (32), with or without a detachable extended stabilizing ring (35), is placed on the skin around the mass which is to be needled, and the needle is guided into the mass accurately as the syringe is held firmly by a syringe body holder (18) which slides on guide bars (46, 30). A vacuum is created by pulling the syringe plunger back with a plunger holder (14), and cells and tissue from the mass are sucked into the syringe as the needle is moved in an up-and-down direction by the hand holding a handlebar (10). The depth of needle penetration is controlled by limit screws (24, 26). When the sample is obtained, the vacuum is released. The needle is removed from skin, and the sample is removed from the syringe.

5 Claims, 5 Drawing Sheets

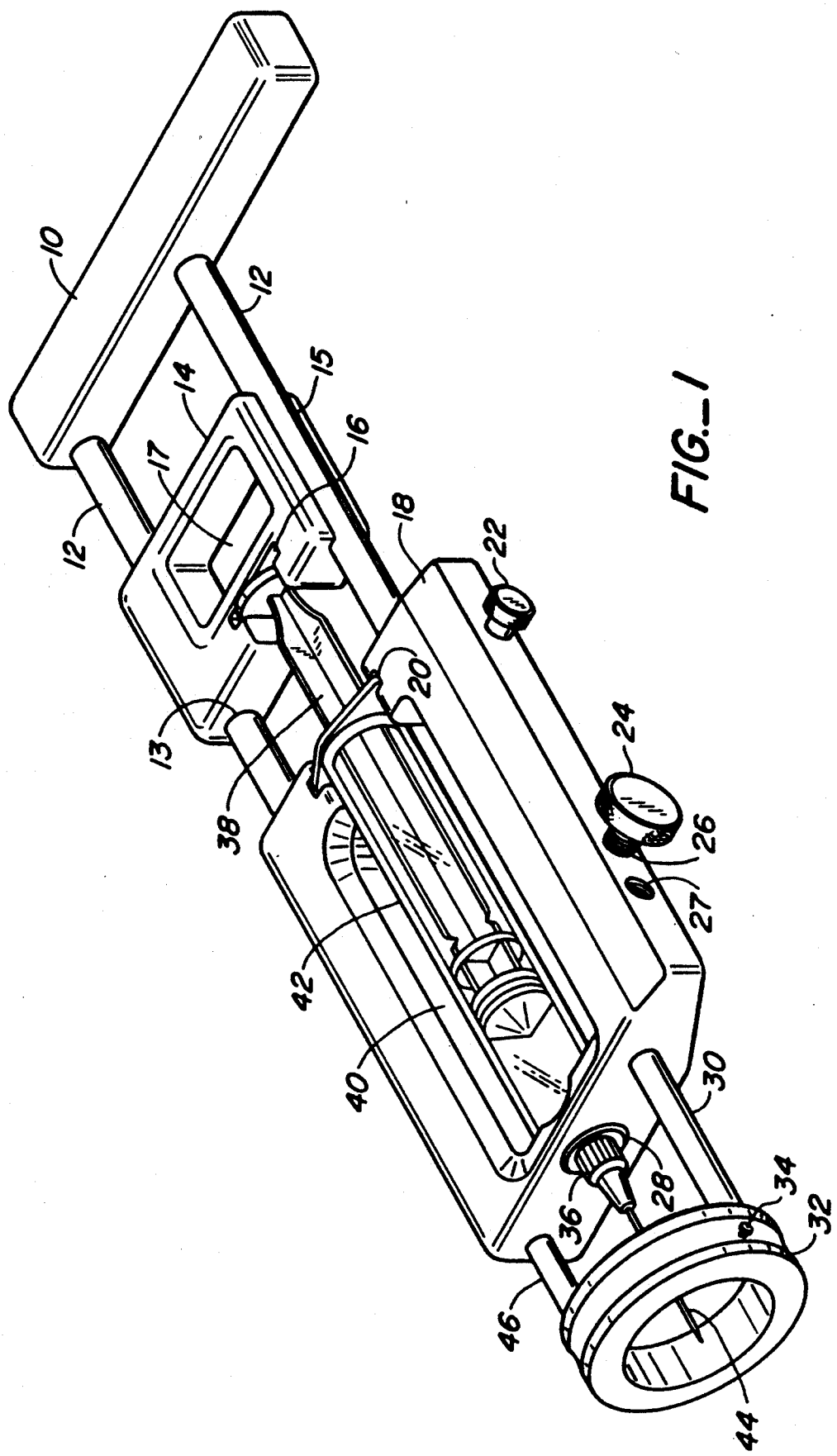
FIG._1

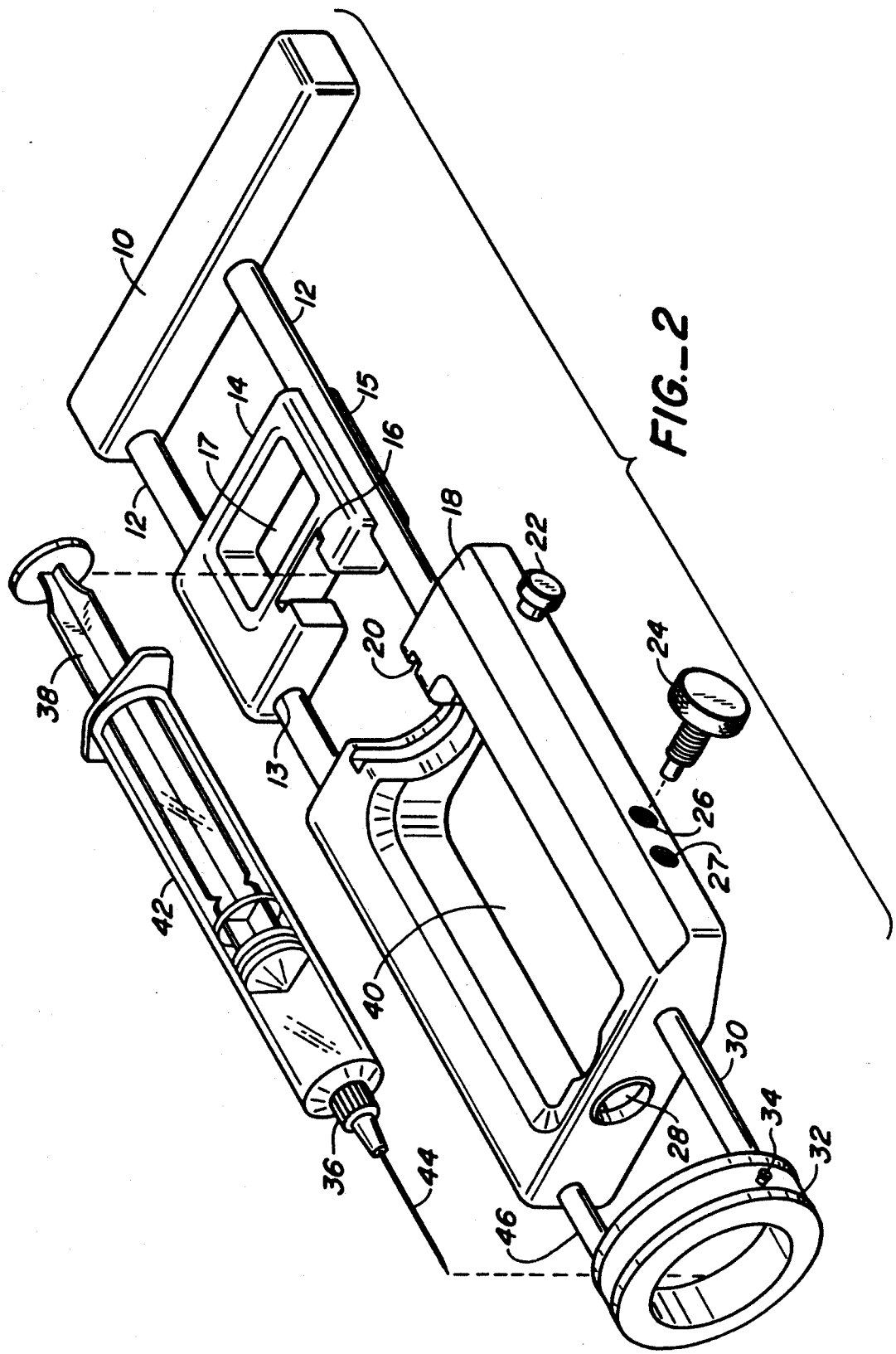
FIG._2

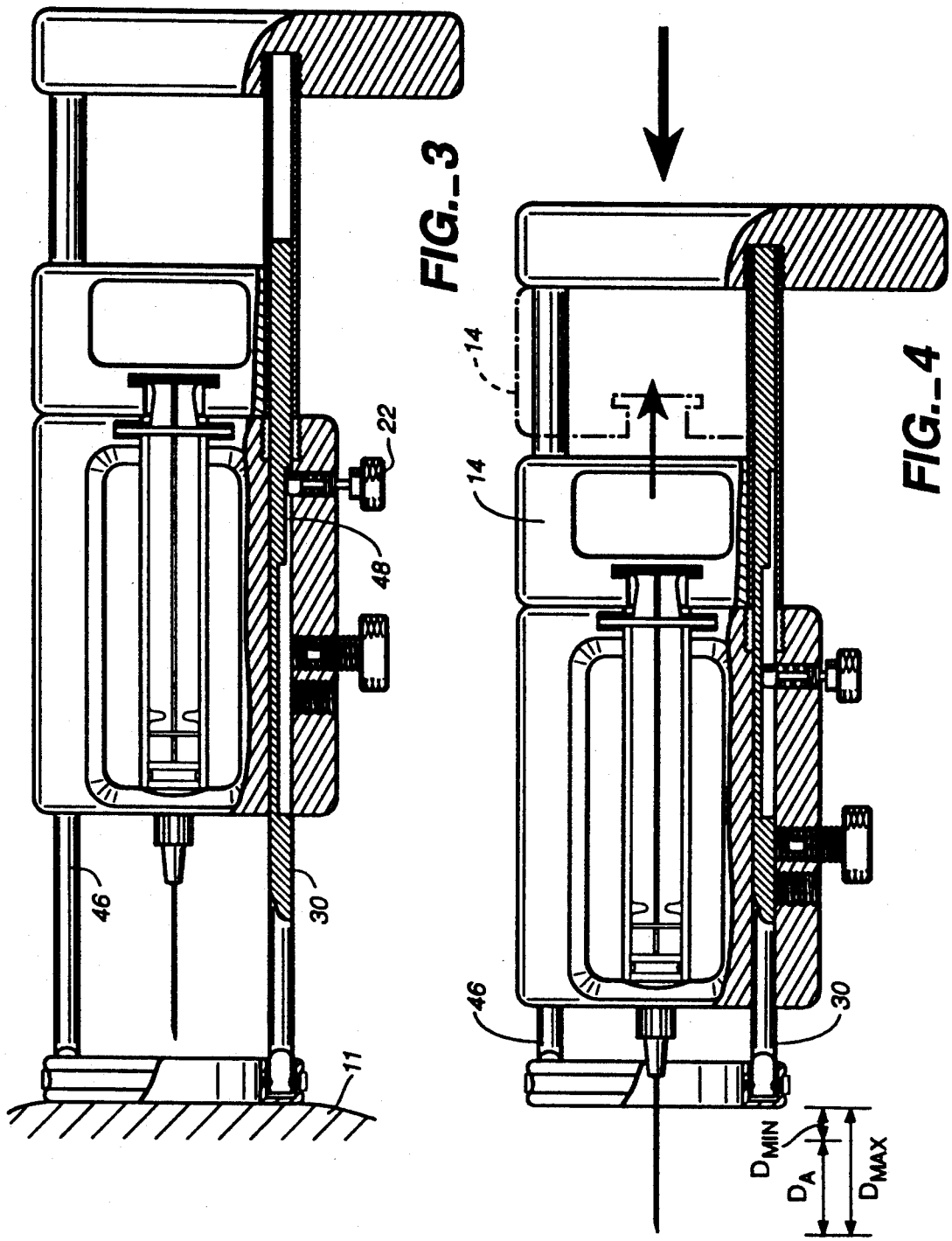

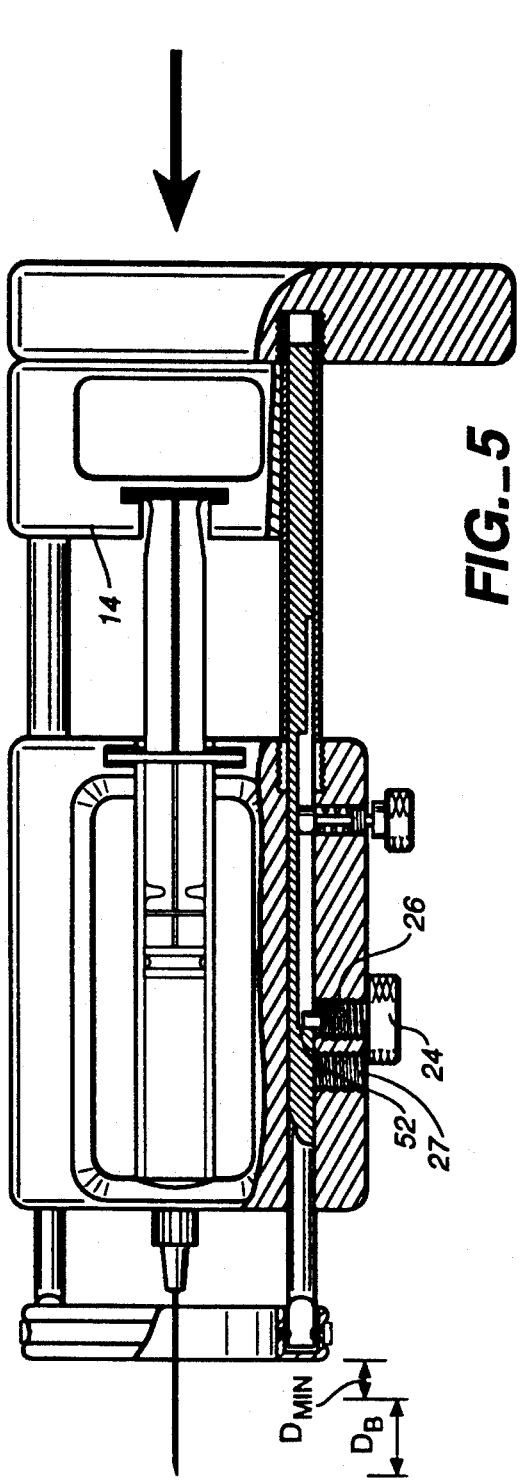
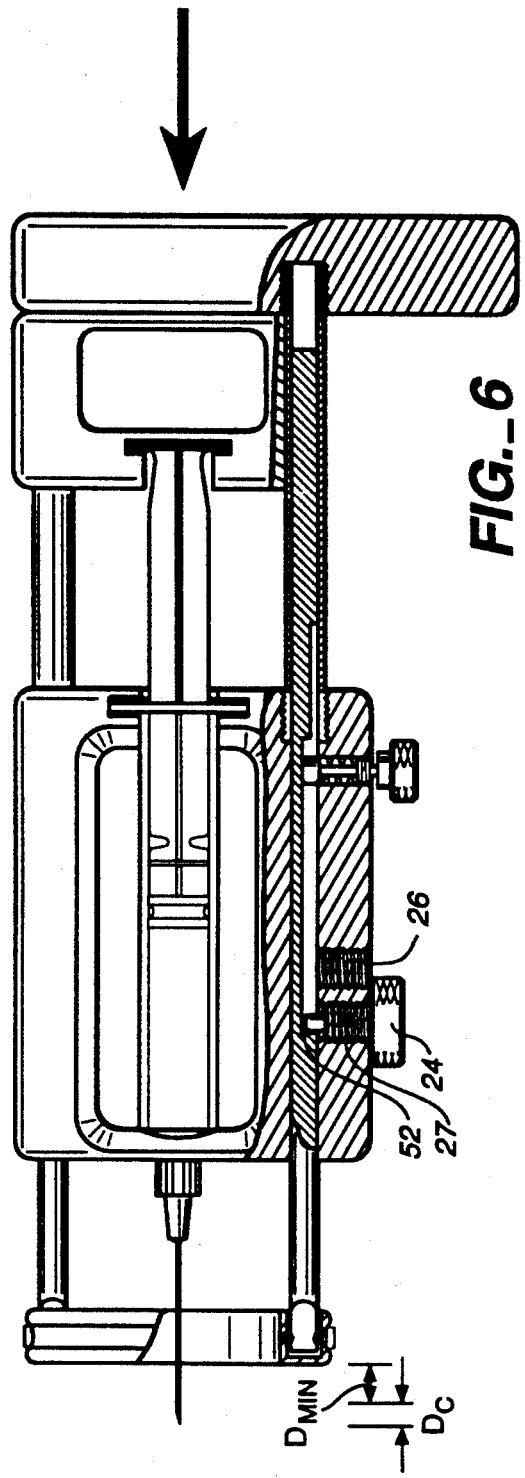

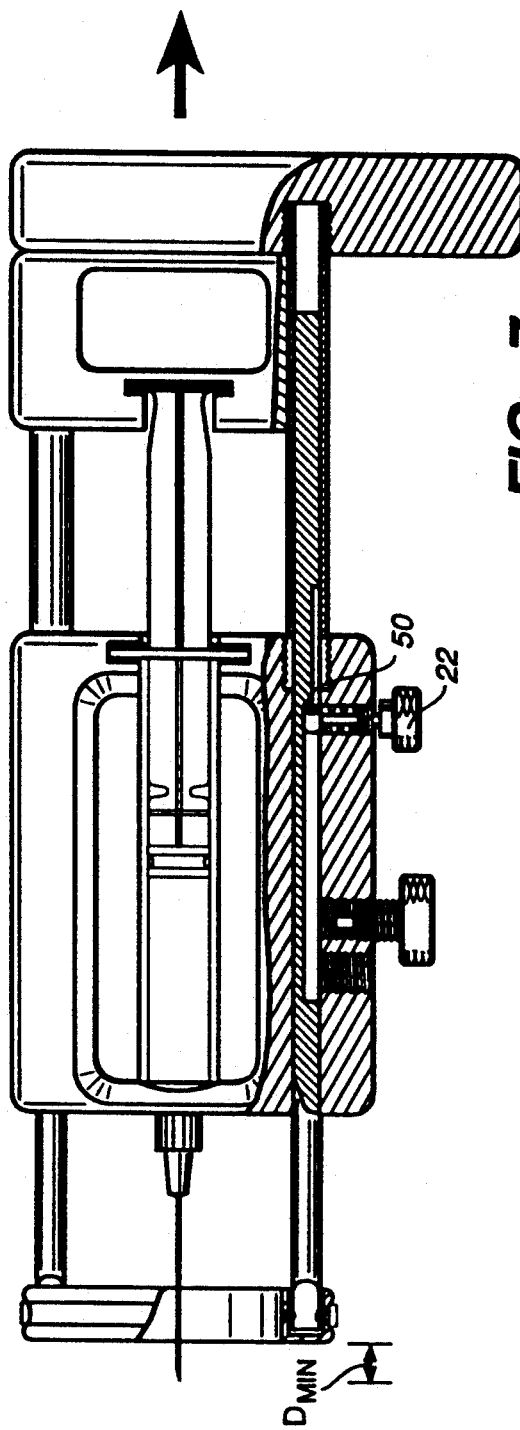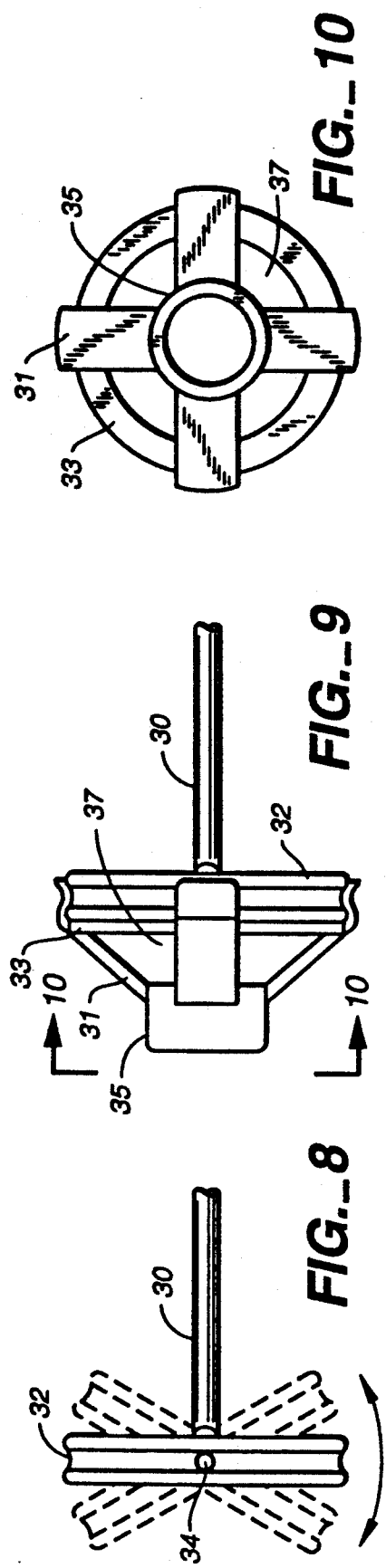

CONTROLLED AND SAFE FINE NEEDLE ASPIRATION DEVICE

BACKGROUND—FIELD OF INVENTION

Our invention relates to medical devices, particularly to fine needle aspiration devices which are used for the removal of human tissue and cells for the diagnosis of cancer and other pathological processes.

BACKGROUND—DESCRIPTION OF PRIOR ART

The pathological diagnostic technique of fine needle aspiration has become widely used in recent years. The technique, which can performed in the doctor's office, allows diagnoses of lesions, such as breast masses. In this technique a fine needle, having an internal diameter of less than 0.5 mm, is inserted through the skin into a palpable ("feelable") mass under the skin, and a vacuum is applied to aspirate or withdraw cells from the mass. The vacuum is created by withdrawing the syringe plunger. During the vacuum state, the user moves the needle up and down with one hand, causing cells and tissue to be cut free so that the vacuum will suck them into the barrel of the syringe. When an adequate sample is obtained, the vacuum is released. The needle is withdrawn, and the material removed is smeared onto glass slides for analysis under a light microscope. Analysis of the material collected provides a means of differentiating between benign processes, such as fibrocystic disease, or malignant processes, such as intraductal carcinoma. In addition, this technique allows diagnosis of other lesions, including thyroid nodules, lung masses, prostate nodules, and enlarged lymph nodes in locations such as the neck, armpit, or groin.

The technique of fine needle aspiration offers multiple advantages over traditional surgical biopsy. Advantages include increased speed of diagnosis, decreased costs (i.e., operating room and recovery room fees), minimized surgical invasiveness, removed risks of surgical anesthesia, and reduced permanent scarring.

Fine needle aspiration usually employs a disable syringe with an attached disposable needle. A syringe holder is presently used with the syringe. The syringe holder is a devices made of a solid material, such as metal, in which the disposable syringe and needle is inserted. The syringe holder allows the user to operate the syringe including withdrawing its plunger with one hand.

Two commonly used syringe holders are (1) the R-H FNA Syringe Holder made by R-H Medical Products of Silver Spring, Md., and (2) the Cameco Syringe Appliance made by Cameco of Sweden. Both are shown in the U.S. Pat. No. 3,819,091 to Hollender (1974). These holders consist of a metal frame with an open center area in which the syringe is inserted. The plunger of the syringe is inserted into another component which slides on a track, allowing withdrawal of the syringe plunger. The device includes a handlebar by which the user holds the device and guides the needle into the skin, withdraws the syringe plunger, and moves the needle up and down.

Three major disadvantages of these prior-art syringe holders are as follows:

(a) They place their users at significant risk of needle-stick accidents. Standard technique with these syringe holders involves localizing the mass with the fingers of one hand while the needle is brought to the skin with the other hand using the syringe holder. Because of the proximity of the fingers to the needle, and the reciprocating motion of the syringe caused by the operator's hand, the operator's fingers can be accidentally stuck by the needle, thereby inoculating the patient's body fluid, cells, or blood into the operator. This may have serious consequences, including infection with viruses, including Hepatitis B, Hepatitis C, or the Human Immunodeficiency Virus (HIV), the etiologic agent causing AIDS.

(b) These syringe holders provide no control mechanism for the oscillating distance of the needle, so that specimen sampling is inaccurate. This may delay expedient diagnosis of cancer and may cause the patient to undergo more invasive and costly procedures to obtain the same diagnosis.

(c) During the reciprocating motion, the needle can unintentionally be withdrawn from the skin, allowing air into the syringe and thereby diluting the specimen sample over the syringe's entire inner surface. This makes removal of the specimen from the syringe for processing difficult so that optimum specimen quality is often reduced. Users have lost many specimens because of this design defect in these syringe holders. When the aspiration is completed, the syringe plunger is released so that the vacuum state of the syringe is relieved. This pressure release is an important step to obtain the specimen sample for optimum slide preparation.

OBJECTS AND ADVANTAGES

Accordingly several objects and advantages of our invention are:

(a) to provide reduced risk of needle-stick accidents by the user of fine needle aspiration devices and thus reduce the risk of accidental infection with infectious agents, such as Hepatitis B, Hepatitis C, and HIV (AIDS);

(b) to provide more accurate diagnosis of tissue samples obtained by fine needle aspiration by allowing more accurate, controlled sampling;

(c) to provide reduced medical costs by eliminating further, often expensive diagnostic techniques, such as diagnostic surgical biopsies, because of a higher percentage of diagnoses obtained on an initial fine needle aspiration procedure;

(d) to provide reduced risk to patients by reducing the need for more invasive diagnostic techniques involving anesthesia, surgical procedures and radiation exposure in X-ray studies;

(e) to reduce scarring resulting from more invasive surgical diagnostic procedures; and (f) to reduce loss of specimens in fine needle aspiration by preventing accidental withdrawal of the needle from the skin when suction is still present in the syringe.

Additional objects and advantages certainly arise from the ability to obtain more accurate diagnoses. The implications of this extend into issues such as time and cost savings for patients and caregivers, earlier diagnosis and treatment of cancer, and overall an increased quality of health care.

Further objects and advantages will become apparent from a consideration of the ensuing description and drawings.

BRIEF DESCRIPTION OF FIGURES

FIG. 1 is a perspective view of an aspiration device according to our invention with a disposable syringe in an operative position.

FIG. 2 is a perspective view with a lower limit screw and the disposable syringe removed.

FIG. 3 is a side view of the device resting on a skin surface with guide bars fully extended.

FIG. 4 is a side view similar to FIG. 3, except the guide bars are fully inserted.

FIG. 5 is a side view of the syringe plunger fully pulled and a lower limit screw in an upper screw hole.

FIG. 6 is a side view showing the lower limit screw in a lower screw hole.

FIG. 7 is a side view showing the lower limit screw partially removed.

FIG. 8 is a side view showing the insertion of one of the guide bars into a stabilizing ring.

FIG. 9 is a side view of the stabilizing ring and guide bars with an extended stabilizing ring attached.

FIG. 10 is an underside view of an extended stabilizing ring with attachment bars and an attachment ring.

REFERENCE NUMERALS IN DRAWINGS

| | |
|---|---|
| 10 handlebar | 31 attachment bar |
| 11 skin | 32 stabilizing ring |
| 12 plunger holder guide | 33 attachment ring |
| 13 plunger holder tube | 34 pivot screw |
| 14 plunger holder | 35 extended stabilizing ring |
| 15 semicircular groove | 36 tip of syringe |
| 16 plunger slit | 37 extended ring space |
| 17 plunger holder cutout | 38 syringe plunger |
| 18 syringe body holder | 40 syringe holder cutout |
| 20 syringe top slit | 42 disposable syringe |
| 22 upper limit spring screw | 44 needle |
| 24 lower limit screw | 46 guide bar |
| 26 upper screw hole | 48 bar retaining indentation |
| 27 lower screw hole | 50 upper limit bar indentation |
| 28 hole for syringe base | 52 lower limit bar indentation |
| 30 guide bar with indentations | |

DETAILED DESCRIPTION OF FIGURES

Overall: A fine needle aspiration device comprises a syringe body holder 18 and a disposable syringe 42 mounted in the holder. Holder 18 comprises handlebar 10 and a stabilizing ring 32 attached respectively to plunger holder guides 12 and guide bars 30 and 46. A translatable plunger holder 14 and syringe body holder 18 are positioned between handle 10 and ring 32.

Handlebar: Handlebar 10 extends perpendicular to the direction of elongation of the device and is attached to two hollow plunger holder guides 12. Guides 12 are about 50 mm apart and handlebar 10 is about 100 mm long. The guides are attached asymmetrically to the handlebar so that a portion of handlebar projects to the upper right of the guides as illustrated. In the preferred embodiment, handlebar 10 is of a solid metal or plastic, such as aluminum, stainless steel, or acrylic. Plunger holder guides 12 are also preferably of a similar solid material which are attached to handlebar 10 permanently through a screw mechanism or welding (not shown).

Plunger Holder: Plunger holder 14 encircles one of plunger holder guides 12, i.e., the guide which is farthest away from the projecting end of handlebar 10. A cylindrical hole in plunger holder 14 forms a plunger holder tube 13. The diameter of plunger holder tube 13 is slightly larger than the diameter of guide 12 which it encircles.

The plunger holder guide 12 closest to the projecting end of handlebar 10 is encircled only halfway by a semicircular groove 15 in the side of plunger holder 14. The diameter of this semicircular groove is slightly larger than the diameter of guide 12 which it partially encircles. The plunger holder has a cutout 17 whose width is slightly less than the distance between two plunger holder guides. A plunger slit 16 is formed in the lower portion of plunger holder 14 extending through the thickness of plunger holder 14. The portion of slit 16 closest to plunger holder cutout 17 is slightly larger than the diameter of the very end of a syringe plunger 38. The slit 16 is slightly larger than the body of syringe plunger 38. This device accommodates a standard disposable syringe made of plastic available from different companies, such as Becton Dickinson & Company (BD) of Rutherford, N.J. E.g., one suitable syringe is BD 10 cc disposable syringe which may be used with a standard BD disposable needle of gauge #21 to #26, with an outside diameter of about 1.0 mm and inside diameter of about 0.5 mm.

Syringe Body Holder: Syringe body holder 18 is rectangular with an elongated central cutout 40. Cutout 40 is wider than syringe 42. A syringe top slit 20 extends around a groove extending on the three sides in the end of the holder 18 closest to handlebar 10. The slit 20 is dimensioned to receive the flange at the top of the syringe 42. Cutout 40 is wider than the standard disposable syringe and begins just below the syringe top slit and end near the other ends of the disposable syringe. The end of the syringe to which a needle 44 is attached protrudes through a hole 28 in the end of the syringe holder. The hole 28 is slightly larger than a tip 36 of syringe 42.

Plunger holder guides 12 are inserted permanently into syringe body holder 18 through welding or a screw mechanism (not shown). The lumens of guides 12 communicate with the hollow areas inside of syringe body holder 18 as seen in FIGS. 3, 4, 5, 6 and 7. A first guide bar 46 (FIG. 3) is slightly smaller in diameter than the inside of the plunger holder guides and syringe holder hollow areas and extends into these tubes through a hole in the ends of the syringe holder. A second guide bar 30 with indentations is positioned similarly to guide bar 46. The indentations are depicted in FIGS. 3, 4, and 5 and are located in the midportion of guide bar 30. The bar retaining indentation is located on the portion of the guide bar nearest to handlebar 10, and a lower limit indentation 52 (FIG. 6) is positioned just below. The indentations are made according to the size of disposable syringe 42 and needle 44.

Limit Screws: An upper limit spring screw 22 is threaded into a hole in the side of syringe body holder 18. Screw 22 communicates with the hollow tube in the syringe holder. A lower limit screw 24 is threaded into either an upper screw hole 26 or a lower screw hole 27. Screw holes 26 and 27 communicate with the hollow space in the syringe holder. Lower limit screw 24 rests within lower limit bar indentation 52 and almost contacts guide bar 30.

Guide bar 46 and guide bar 30 are attached to stabilizing ring 32 through pivot screws 34. Ring 32 is made of a solid material and has an indentation circumferentially around the outside diameter. The inside diameter may vary widely from 10 to 50 mm. Needle 44 is in the center of ring 32.

Stabilizing Ring: As shown in FIGS. 9 and 10, an extended stabilizing ring 35 is attached to stabilizing ring 32 via four attachment bars 31. An attachment ring 33 with diameters of the same inner and outer diameter of stabilizing ring 32 and a thicknes of approximately 2 mm rests on stabilizing ring 32 and is attached permanently to attachment bars 31. Extended stabilizing ring 35 has smaller inner and outer diameters than stabilizing ring 32. The inner diameter may vary from 5 to 35 mm. Attachment bars 31 are attached permanently to extended stabilizing ring 35 and are oriented outward at an angle away from extended stabilizing ring, thereby forming extended ring space 37. Attachment bars 31 extend outward to a distance slightly greater than the outer diameter of stabilizing ring 32 where they then curve in a sigmoid (S) shape at the tips. The ends of attachment bars 31 conform to the outer diameter edge of stabilizing ring 32.

OPERATION, FIGS. 1 TO 10

To use the fine needle aspiration device, one must first assess the mass under the skin which the user is going to examine. The patient should be first positioned in the usual manner for fine needle aspiration, namely, in a position which allows the easiest access to the lesion. This is especially important if the mass is located in places of more difficult access, such as the armpit. The mass is then palpated thoroughly, and its depth under the skin is estimated. Extended stabilizing ring 35 is used if needed for better localization of small masses. To use ring 35 it is clipped onto stabilizing ring 32.

The user then selects a needle 44 of suitable length to reach the mass. Lower limit screw 24 is placed in one of screw holes 26 or 27. Use of lower screw hole 27 allows penetration 5 mm deeper than $D_{min}$ to a depth $D_C$. (FIGS. 6 and 7). Use of upper screw hole 26 allows penetration 5 mm deeper than depth $D_C$ to a depth $D_B$. (FIG. 5) If the screw is not screwed fully into its hole, the needle will be allowed to penetrate its entire length into the patient's skin. ($D_{max}$, FIG. 4)

Syringe body holder 18, plunger holder 14, plunger holder guides 12, and handlebar 10 all slide over guide bar 46 and guide bar 30. Upper limit screw 22 can be pulled out, and the guide bars can be extended longer. The retaining indentation in bar retaining indentation 30 prevents removal of the guide bars unless upper limit screw 22 is retracted. Upper limit screw 22 is next retracted, and the guide bars are withdrawn until the bar retaining indentation prevents further removal. The needle of choice is then attached to syringe 26, and these are placed in the device. Syringe plunger 38 is slipped into plunger slit 16, but syringe plunger 38 is not yet withdrawn.

Stabilizing ring 32 is next placed on the skin with the center of the mass to be aspirated in the center of stabilizing ring. The upper portion of the device is rotated on stabilizing ring 32 as depicted in FIG. 8 until the appropriate angle for optimum needle access is maintained. After the needle enters the skin, the angle should not be changed appreciably as this may cause tissue shearing and unnecessary bleeding.

The user then holds the device in position by grasping stabilizing ring 32 firmly with the fingers of one hand. The other hand is positioned on handlebar 10 and two fingers from that hand are placed in plunger holder cutout 17. Pressure is exerted downward, and the needle is advanced into the skin to the deepest depth that is allowed by chosen lower limit screw 24. A click will be heard during this movement as upper limit screw 22 is driven with a spring into upper limit indentation 50. This will occur when the needle is just under the skin. Subsequent withdrawal of the needle is prevented by upper limit screw 22 unless upper limit screw is pulled out while the upper portion of the device is being reciprocated.

When needle 44 is in the skin, syringe plunger 38 is pulled by the fingers of the hand on handlebar 10. This creates a vacuum inside syringe 42. The upper portion of the device is then moved up and down repeatedly by movement of the user's hand as it slides along guide bars 46 and 30. This movement is demonstrated in FIG. 5. The movement of the needle under the skin causes cells and tissue to be cut free and sucked into the syringe. The up and down movement is performed about 10 times or until an adequate sample is obtained in the syringe. Local anesthesia is not required because the small bore of the needle causes little discomfort.

When the sample is collected in syringe 42, the syringe plunger 38 is released by releasing syringe plunger 38 from the grasp of the user's fingers. This causes the vacuum in the syringe to be relieved. The entire device is then pulled away from the skin, and needle 44 is withdrawn with this movement. The syringe is then removed quickly from the device. The needle is removed, and the syringe plunger is once again withdrawn. When it is fully withdrawn, the needle is placed back on syringe, and the specimen is expelled from syringe onto glass slides through a quick, forceful push of syringe plunger. The slides are then processed by microscopic examination and subsequent cytological diagnosis.

Additionally, guide bars 46 and 30 with attached stabilizing ring 32 can be removed completely from the other portion of the device. This can be accomplished by pulling upper limit screw 22 and guide bars 36 and 40 out simultaneously. At this point, the mechanism may be used exactly as prior-art devices for fine needle aspiration. This may be necessary occasionally, e.g., if there is a lesion which cannot be optimally accessed using the entire device.

CONCLUSION, RAMIFICATIONS, AND SCOPE OF INVENTION

The reader can see that our fine needle aspiration device of the invention proves an accurate, controlled, and safe means of obtaining tissue from masses for cytological diagnosis of cancer and other pathological processes. The major advantages include the following:

(a) reduced risk of needle stick accidents during the procedure because of better stabilization with stabilizing ring 32 which localizes the lesion and allows the user's fingers to rest on the ring and out of the path of the needle, which is limited to the exact center of the ring;

(b) increased accuracy in obtaining specimens because of the control of needle penetration depth and direction of reciprocation as limited by guide bars 30 and 46;

(c) reduced need for further more invasive procedures, such as surgery, because of the increased accuracy by more controlled sampling;

(d) minimized scarring of the skin because invasive procedures are not necessary as often; and (e) reduced speciman loss from accidental premature withdrawal from the skin because of upper limit screw 22.

While the above description contains many specificities, they should not be construed as limitations on the scope of the invention, but rather as an exemplification of one preferred embodiment thereof. Many other variations are possible. Namely, different sizes may be constructed which accommodate different sizes of syringes and needles. For example, a larger model may be useful in fine needle aspiration of masses deep in the body, such as in the lungs or liver. The localization for this type of use requires (as it does now) concurrent radiological localization using a CAT scan or ultrasound. An electrically operated mechanism can also be attached to withdraw the syringe plunger and provide the oscillating motion.

Thus the scope of the invention should be determined by the appended claims and their legal equivalents, rather than by the examples given.

We claim:

1. In a manually operated device for aspirating body cells into a hypodermic needle syringe, said device including a syringe holder to hold a syringe having a hypodermic needle and a plunger, said syringe holder having a syringe flange holding means and an opening to receive said hypodermic needle; a syringe plunger holder mounted on parallel guides to move relative to said syringe holder in a direction axial to said syringe and a handlebar mounted on said parallel guides, spaced from said syringe holder and with said plunger holder positioned between said syringe holder and said handlebar; the improvement comprising:

parallel guide bars slidably mounted in passageways in said syringe holder with one end of each of said guide bars extending from said syringe holder, a stabilizing ring connected to the extended ends of said guide bars and positioned to surround the longitudinal axis of said needle, an indentation in one of said guide bars, a limit means on said syringe holder positioned to enter said indentation to limit the minimum extension of said guide bars from said syringe holder.

2. The device of claim 1 wherein said stabilizing ring is pivotably attached to said guide bars.

3. The device of claim 1 wherein one of said guide bars includes a second indentation to receive a second limit means which prevents said guide bar from sliding out of said passageway.

4. The device of claim 1 wherein said stabilizing ring is rotatably mounted to said extending ends of said guide bars.

5. The device of claim 1 including an extended stabilizing ring spaced from and releasably attached to said stabilizing ring.

* * * * *